United States Patent
Cramer et al.

(10) Patent No.: US 10,132,763 B2
(45) Date of Patent: Nov. 20, 2018

(54) INSPECTION METHOD AND APPARATUS, LITHOGRAPHIC SYSTEM AND DEVICE MANUFACTURING METHOD

(71) Applicant: ASML Netherlands B.V., Veldhoven (NL)

(72) Inventors: Hugo Augustinus Joseph Cramer, Eindhoven (NL); Robert John Socha, Campbell, CA (US); Patricius Aloysius Jacobus Tinnemans, Hapert (NL); Jean-Pierre Agnes Henricus Marie Vaessen, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 14/416,484

(22) PCT Filed: Jun. 18, 2013

(86) PCT No.: PCT/EP2013/062630
§ 371 (c)(1),
(2) Date: Jan. 22, 2015

(87) PCT Pub. No.: WO2014/016056
PCT Pub. Date: Jan. 30, 2014

(65) Prior Publication Data
US 2015/0177166 A1 Jun. 25, 2015

Related U.S. Application Data

(60) Provisional application No. 61/730,474, filed on Nov. 27, 2012, provisional application No. 61/674,505, filed on Jul. 23, 2012.

(51) Int. Cl.
*G03B 27/52* (2006.01)
*G01N 23/203* (2006.01)
(Continued)

(52) U.S. Cl.
CPC ....... *G01N 23/203* (2013.01); *G03F 7/70058* (2013.01); *G03F 7/70625* (2013.01); *H01J 37/26* (2013.01)

(58) Field of Classification Search
CPC ................... G03F 7/70058; G03F 7/70625
(Continued)

(56) References Cited

U.S. PATENT DOCUMENTS 5,900,633 A 5/1999 Solomon et al.
6,421,457 B1 7/2002 Su
(Continued)

FOREIGN PATENT DOCUMENTS

EP 1 628 164 A2 2/2006
JP 2004/510152 A 4/2004
(Continued)

OTHER PUBLICATIONS

Dasari, P., et al., "Metrology Characterization of spacer double patterning by scatterometry," Proceedings of SPIE: Metrology, Inspection, and Process Control for Microlithography XXV, vol. 7971, 2011; pp. 797111-1 to 797111-12.
(Continued)

*Primary Examiner* — Hung Henry Nguyen
(74) *Attorney, Agent, or Firm* — Sterne, Kessler, Goldstein & Fox P.L.L.C.

(57) ABSTRACT

An inspection method determines values of profile parameters of substrate patterns. A baseline substrate with a baseline pattern target (BP) is produced that has a profile described by profile parameters, for example CD (median critical dimension), SWA (side wall angle) and RH (resist height). Scatterometry is used to obtain first and second signals from first and second targets. Values of differential pattern profile parameters are calculated using a Bayesian differential cost function based on a difference between the
(Continued)

baseline pupil and the perturbed pupil and dependence of the pupil on pattern profile parameters. For example, the difference is measured between a baseline process and a perturbed process for stability control of a lithographic process. Fedforward differential stack parameters are also calculated from observations of stack targets on the same substrates as the pattern targets.

16 Claims, 7 Drawing Sheets

(51) Int. Cl.
  *G03F 7/20* (2006.01)
  *H01J 37/26* (2006.01)
(58) Field of Classification Search
  USPC .......................................... 355/52, 53, 55, 67
  See application file for complete search history.

(56) References Cited

U.S. PATENT DOCUMENTS

| | | | |
|---|---|---|---|
| 7,065,737 B2 | 6/2006 | Phan et al. | |
| 7,099,005 B1 | 8/2006 | Fabrikant et al. | |
| 7,273,685 B2 | 9/2007 | Sasazawa et al. | |
| 7,352,453 B2 * | 4/2008 | Mieher | G01N 21/956 356/125 |
| 7,619,737 B2 | 11/2009 | Mos et al. | |
| 7,916,284 B2 | 3/2011 | Dusa et al. | |
| 7,933,016 B2 * | 4/2011 | Mieher | G01N 21/956 356/401 |
| 8,035,824 B2 | 10/2011 | Ausschnitt | |
| 9,128,065 B2 | 9/2015 | Cramer et al. | |
| 2004/0039473 A1 | 2/2004 | Bao et al. | |
| 2006/0160001 A1 | 7/2006 | Wang | |
| 2006/0183040 A1 | 8/2006 | Hideaki et al. | |
| 2008/0007739 A1 | 1/2008 | Vuong et al. | |
| 2008/0248403 A1 * | 10/2008 | Yu | G03F 7/70625 430/5 |
| 2009/0063077 A1 | 3/2009 | Liu et al. | |
| 2010/0328655 A1 | 12/2010 | Den Boef | |
| 2011/0027704 A1 * | 2/2011 | Cramer | G03F 7/70641 430/30 |
| 2011/0043791 A1 | 2/2011 | Smilde et al. | |

FOREIGN PATENT DOCUMENTS

| | | |
|---|---|---|
| JP | 2007/528126 A | 10/2007 |
| KR | 1020080069136 A | 7/2008 |
| KR | 1020100091919 A | 8/2010 |

OTHER PUBLICATIONS

Finders, J., et al., "Double pattering for 32nm and below: an update," Proceedings of SPIE: Optical Microlithography XXI, 2008; pp. 692408-1 to 692408-12.

Henn, M.-A., et al., "Improved geometry reconstruction and uncertainty evaluation for extreme ultraviolet (EUV) scatterometry based on maximum likelihood estimation," Proceedings of SPIE: Modeling Aspects in Optical Metrology III, 2011; pp. 80830N-1 to 80830N-10.

International Search Report directed to related International Patent Application No. PCT/EP2013/062630, dated Dec. 18, 2013; 3 pages.

International Preliminary Report on Patentability and Written Opinion of the International Searching Authority directed to related International Patent Application No. PCT/EP2013/062630, dated Jan. 27, 2015; 7 pages.

Translation of Japanese Search Report by Registered Searching Authority, directed to related Japanese Patent Publication No. 2015/525902 A, dated Jan. 20, 2016; 23 pages.

* cited by examiner

INSPECTION METHOD AND APPARATUS, LITHOGRAPHIC SYSTEM AND DEVICE MANUFACTURING METHOD

CROSS-REFERENCE TO RELATED APPLICATIONS

This application claims the benefit of U.S. provisional application 61/674,505, which was filed on Jul. 23, 2012, and of U.S. provisional application 61/730,474, which was filed on Nov. 27, 2012, and which are incorporated herein in its entirety by reference.

BACKGROUND

Field of the Invention

The present invention relates to methods of inspection usable, for example, in the manufacture of devices by lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor and control the lithographic process, it is necessary to measure parameters of the patterned substrate, for example the linewidth (Critical Dimension) and sidewall angle (SWA) of features formed in or on it. There are various techniques for making measurements of the microscopic structures (features) formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the properties of the beam (intensity, polarization state) as a function of wavelength of the radiation scattered into a particular narrow angular range. Angularly resolved scatterometers use a monochromatic radiation beam and measure the properties of the scattered radiation as a function of angle of the reflected beam.

The target may be specially formed for the purposes of the monitoring and control measurements. Alternatively the target may be present already in product features being formed on the substrate. The target may be formed of resist material that has been patterned by the lithographic process, prior to etching of the substrate material. The resist material may or may not have been developed. Irrespective of these details of implementation, we can say the measurements seek to measure one or more parameters that characterize the target, such as parameters that describe the profile or shape of the target. For control of a lithographic process, a change in target profile may be used to control the lithographic apparatus (scanner). The change in target profile is from a reference process to a perturbed process. The reference process may be for example the process at a certain time on a certain apparatus, the process of an individual apparatus with the best yield, or the process in which an OPC (Optical Proximity Correction) model was created. The perturbed process may be a process exposed at a different time or on a different lithographic apparatus or coating/developing apparatus (referred to in the art as the "track"). The perturbed process may be implemented side-by-side with the reference process by introducing targets with biased parameters. Both processes may in fact be biased relative to an ideal process, so that the terms "reference" and "perturbed" are merely labels and are interchangeable for the purposes of the measurement itself. In known approaches to calculate the change in target profile, the absolute target profile is calculated for the reference process. Next the absolute target profile is calculated for the perturbed process. The change in target profile is then obtained by subtraction of these two absolute profiles. Such a method is a biased predictor of the change because one has to use prior information for the reconstruction of the profile based on observations made by scatterometry. Any metrology method that is biased has inherent problems in the confidence of the measurement. In addition, the creation of a recipe to measure the absolute target profile is a tedious job, requiring a skilled and experienced engineer.

SUMMARY

It is desirable to improve the accuracy of the change in profile between the reference and perturbed process.

According to a first aspect of the present invention, there is provided an inspection method for determining values of profile parameters of substrate patterns, the method comprising the steps: supporting a substrate comprising a first pattern target; illuminating the first pattern target with radiation and detecting scattered radiation to obtain a first pattern signal; supporting a substrate comprising a second pattern target; illuminating the second pattern target with radiation and detecting scattered radiation to obtain a second pattern signal; and calculating values of differential pattern profile parameters using a difference between the first pattern signal and the second pattern signal.

In terms of the introductory discussion above, one of the first and second pattern targets may be a target produced by the reference process, while the other is a target produced by the perturbed process. The differential pattern profile parameters can then be used directly or indirectly to reveal differences between those processes.

When referring to the "difference" between signals, it should be understood that this encompasses a ratiometric (percentage) difference, not only a different obtained by subtraction. The skilled person can choose the correct comparison technique, and the most appropriate manner of representing differences.

Depending on the application, the substrate with the first pattern target may be the same as or different from the substrate with the second pattern target. For example, where the targets are on different substrates, the differential profile parameters may be used to reveal a difference between processes executed on different apparatus, and/or processes executed at different times. Where the first pattern target and the second pattern target are both on the same substrate, the differential profile parameters may be used to reveal a difference between processes executed at different locations on the same substrate or within a portion of the substrate. Alternatively, the first pattern target and second pattern targets may be a pair of differently biased targets, formed by a common process at substantially the same position on the same substrate. Differently biased targets in this context means two targets designed so that their profile parameters have different sensitivities to a parameter of interest in a process by which they were formed.

According to a second aspect of the present invention, there is provided inspection apparatus for determining values of profile parameters of substrate patterns, the inspection apparatus comprising: a support for a substrate; an optical system configured to illuminate one or more pattern targets on the substrate with radiation and detect scattered radiation to obtain a corresponding pattern signal; and a processor arranged to calculate values of differential pattern profile parameters using a difference between a first pattern signal detected from a first pattern target using the optical system and a second pattern signal detected from a second pattern target using the optical system.

According to a third aspect of the present invention, there is provided a computer program product comprising machine-readable instructions for causing a processor to perform the step (e) of a method according to the first aspect.

According to a fourth aspect of the present invention, there is provided a lithographic system comprising: a lithographic apparatus comprising: an illumination optical system arranged to illuminate a pattern; a projection optical system arranged to project an image of the pattern onto a substrate; and an inspection apparatus according to the second aspect, wherein the lithographic apparatus is arranged to use the measurement results from the inspection apparatus in applying the pattern to further substrates.

According to a fourth aspect of the present invention, there is provided a method of manufacturing devices wherein a device pattern is applied to a series of substrates using a lithographic process, the method including inspecting at least one periodic structure formed as part of or beside said device pattern on at least one of said substrates using a method according to the first aspect and controlling the lithographic process for later substrates in accordance with the result of the method.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
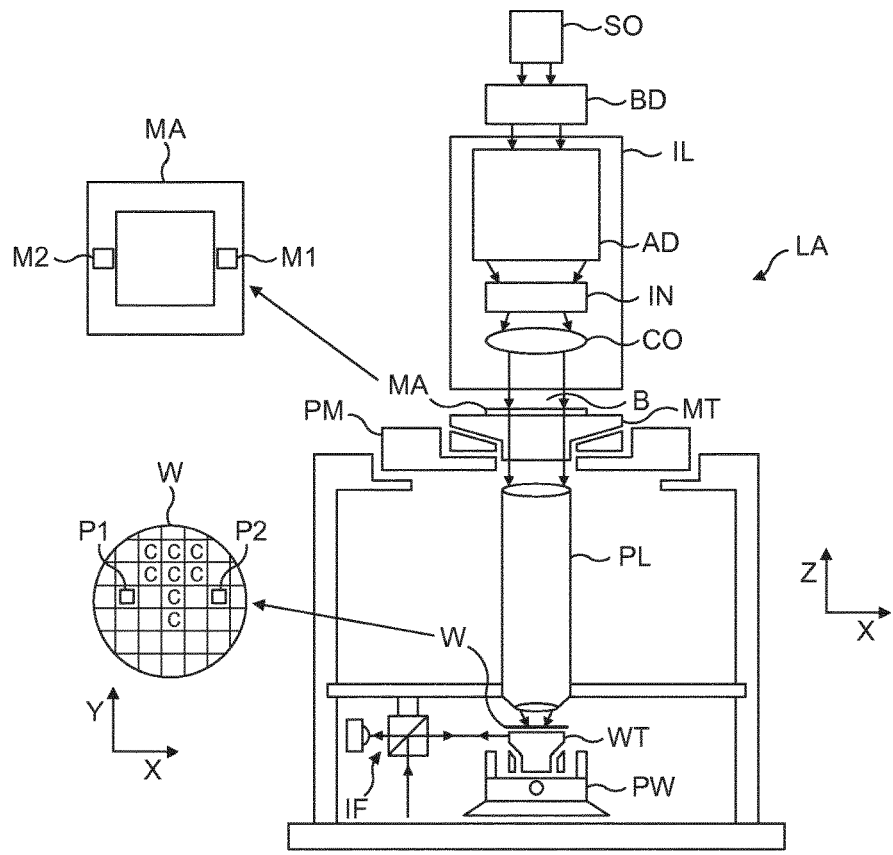
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation). A support structure (e.g., a mask table) MT constructed to support a patterning device (e.g., a mask) MA and connected to a first positioner PM configured to accurately position the patterning device in accordance with certain parameters. A substrate table (e.g., a wafer table) WT constructed to hold a substrate (e.g., a resist-coated wafer) W and connected to a second positioner PW configured to accurately position the substrate in accordance with certain parameters. A projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:
1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
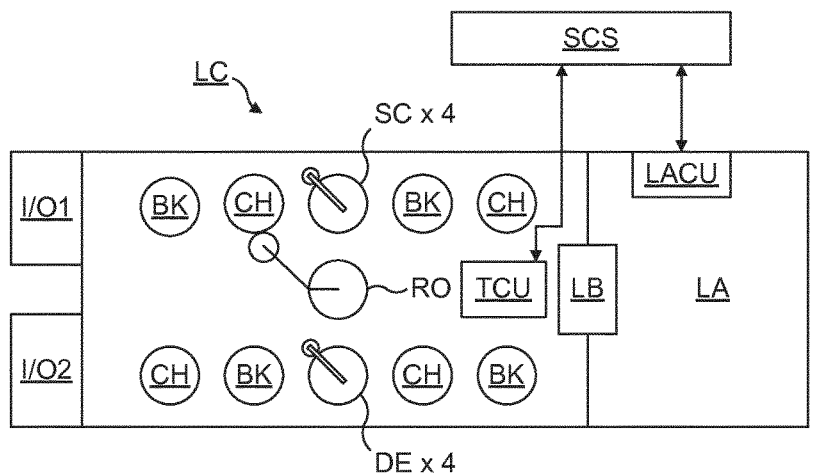
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
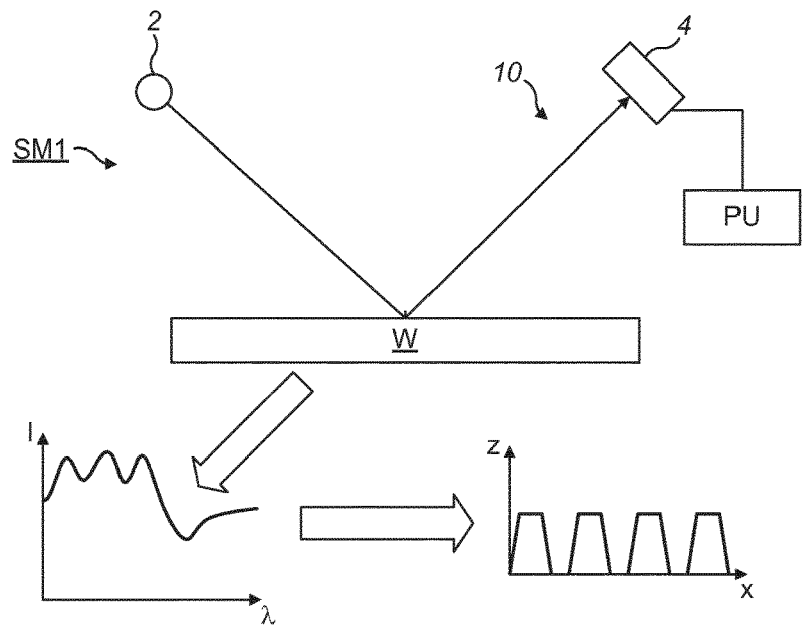
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
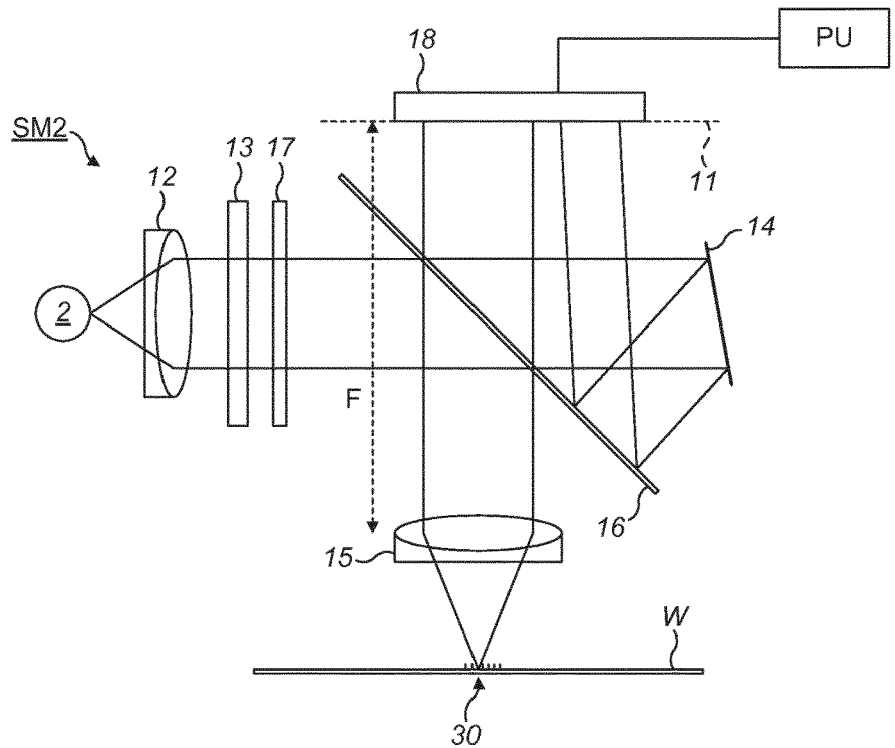
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in European patent application EP1,628,164A, which is incorporated by reference herein in its entirety.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
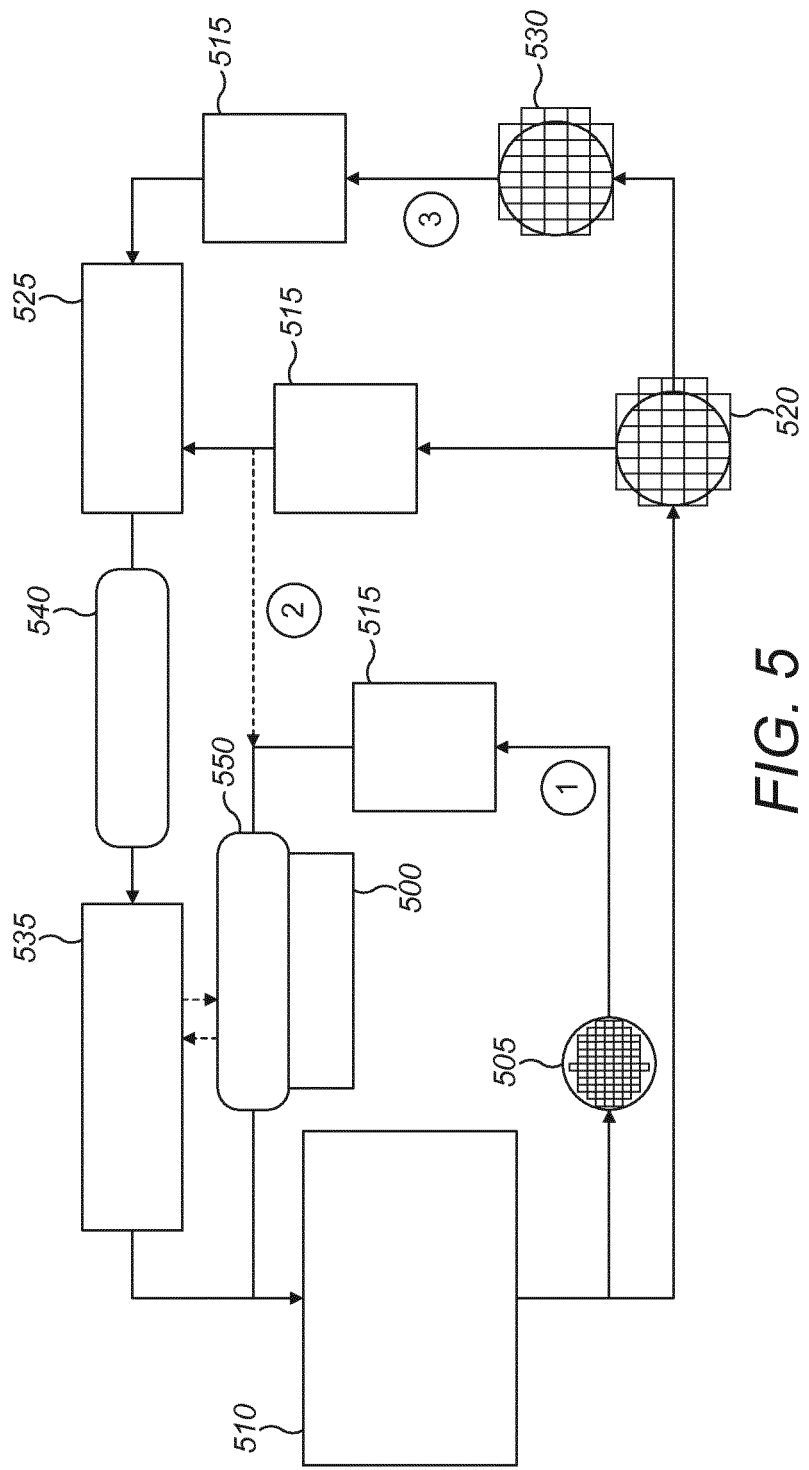
FIG. 5 illustrates the control loops in a lithographic process utilizing a scanner stability module.

FIG. 5 depicts an overall lithography and metrology system incorporating a scanner stability module 500 (essentially an application running on a server, in this example). Shown are three main process control loops. The first loop provides the local scanner control using the scanner stability module 500 and monitor wafers. The monitor wafer 505 is shown being passed from the main lithography unit 510, having been exposed to set the baseline parameters for focus and overlay. At a later time, metrology unit 515 reads these baseline parameters, which are then interpreted by the scanner stability module 500 so as to calculate correction routines 550 which are passed to the main lithography unit 510, and used when performing further exposures.

The second Advanced Process Control (APC) loop is for local scanner control on-product (determining focus, dose, and overlay). The exposed product wafer 520 is passed to metrology unit 515 and then onto the Advanced Process Control (APC) module 525. Data from the metrology unit 515 is again passed to the scanner stability module 500. Process corrections 540 are made before the Manufacturing Execution System (MES) 535 takes over, providing scanner control to the main lithography unit 510, in communication with the scanner stability module 500.

The third loop is to allow metrology integration into the second APC loop (e.g., for double patterning). The post etched wafer 530 is passed to metrology unit 515 and then onto the Advanced Process Control (APC) module. The loop continues the same as with the second loop.

As mentioned in the introduction, the principle of obtaining differential profile parameters from first and second pattern signals can be applied in a wide range of situations. The scatterometer of FIG. 4 will be used as an example of the instrument for use in the method. The pupil image captured by the detector from a target 30 is an example of the pattern signal referred to in the introduction. A first example will now be described in more detail, with particular reference to the comparison of baseline and perturbed processes. This may be used directly in implementing the stability control loop of FIG. 5. A second example, described further below, relates to balancing of spacing in a so-called double patterning process. These are just examples, and not limiting on the scope of the invention.

In the first example, for control of a lithographic process a change in target profile may be calculated directly from first and second pattern signals, rather than an absolute target profile. The target may be a grating formed in exposed resist material an the target profile may be referred to also as a "resist profile". Embodiments of the present invention use pattern signals in the form of angularly resolved scatterometer pupils from two pattern targets. The pattern targets may for example be a reference target representing a baseline process and a subject target representing a perturbed process. The change in profile is measured by comparing scatterometer signals from a baseline monitor wafer to signals from a target that was printed with the nominally the same conditions as the baseline wafer but is exposed at a different time, scanner, track, i.e., a perturbed condition. In this example, a differential cost function is described for measuring the profile changes from two scatterometer pupils, the baseline pupil and the perturbed pupil. The scatterometer pupil image is a measured quantity which means that this method is unbiased. The two pupil images are then subtracted, and the change in the target profile is calculated. This greatly reduces the prior information needed for absolute measurement of CD or other parameter. It is replaced by prior information for the difference measurement described herein. For example, a Jacobian is computed based on some initial parameter setting. If this initial parameter setting is far off reality then there may still be a problem. Since it is assumed that the Jacobian is slowly varying for different parameter settings in the regions of interest, the exact initial parameter setting might not be that critical. However, a sensible guess is still used, i.e., prior information. Since the pupil is subtracted, calibration of the scatterometer is less critical. Furthermore, the scatterometer setup recipe creation for change in target profile is easier than the recipe creation for absolute profile measurement because the differential profile requires different, more easily available prior information. The assumed prior information of the change in profile represented by a difference parameter, u, is close to zero The present example improves the accuracy of measuring a change in profile between a baseline process and a perturbed process by using an unbiased technique for differential CD reconstruction. The technique uses an approach known as Bayesian maximum a posteriori estimation, abbreviated to Bayesian-MAP estimation.

Figure 6:
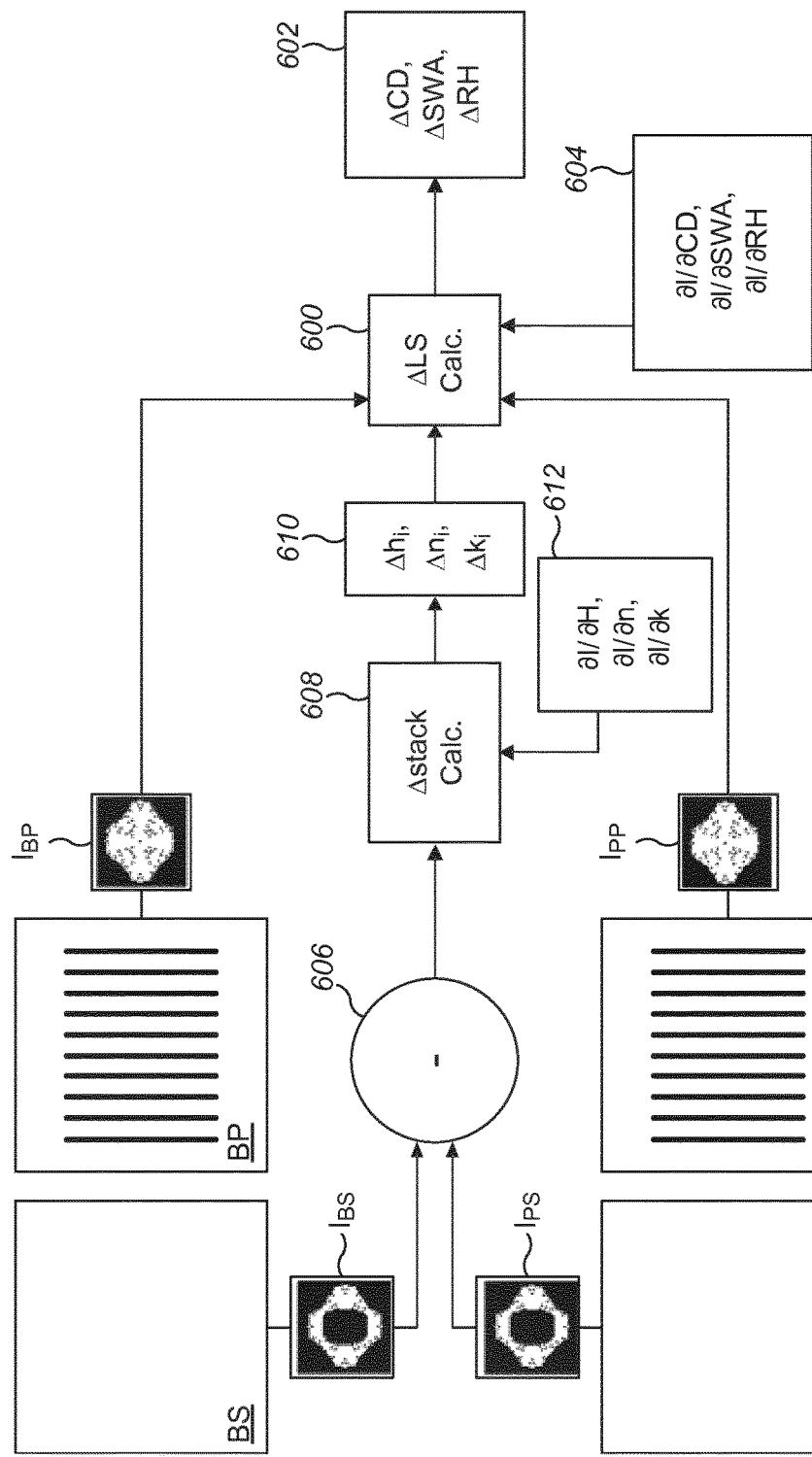
FIG. 6 illustrates an inspection method for determining values of profile parameters of substrate patterns, in accordance with a first embodiment of the present invention.

FIG. 6 illustrates an inspection method for determining values of change or difference in profile parameters of substrate patterns, in the first example. With reference to FIG. 6, the steps are: producing a baseline substrate comprising a baseline pattern target (BP), having a profile described by profile parameters, for example CD (median critical dimension), SWA (side wall angle) and RH (resist height); illuminating the baseline pattern target (BP) with radiation and detecting scattered radiation to obtain a baseline pupil or pattern signal ($I_{BP}$); producing a perturbed substrate comprising a perturbed pattern target (PP), having a profile described by profile parameters, for example CD, SWA and RH; and illuminating the perturbed pattern target (PP) with radiation and detecting scattered radiation to obtain a perturbed pupil or pattern signal ($I_{PP}$). Using the scatterometer of FIG. 4, each pattern signal comprises the two-dimensional set of pixel intensities across the pupil image, for one or more wavelengths of incident radiation.

Because the reference target and subject target in this example may be on different substrates and/or may be formed at different times or on different machines, not only the pattern target but also the underlying layers or "stack" may vary. Such variations may be by design, or they may be the result of process variations. The first example method illustrated in FIG. 6 includes steps for eliminating differences that are caused by differences in the underlying stack, so as to isolate more accurately the difference in the pattern target itself. For this purpose, the baseline substrate also has a baseline stack target (BS), described by stack parameters $H_i$ (layer height or thickness) and complex refractive index parameters $n_i$ (refractive index) and $k_i$ (extinction coefficient) for each layer, i, of the stack. The perturbed substrate also has a perturbed stack target (PS), described by stack parameters $H_i$, $n_i$ and $k_i$ for each layer, i, of the stack. These stack targets are effectively just blank portions of the substrate that may be beside the corresponding pattern target, and are identical except for the lack of the pattern target. The method of the example further includes: illuminating the baseline stack target (BS) with radiation and detecting scattered radiation to obtain a baseline stack signal ($I_{BS}$); and illuminating the perturbed stack target (PS) with radiation and detecting scattered radiation to obtain a perturbed stack signal ($I_{PS}$).

The method then comprises calculating (600) values of one or more differential pattern profile parameters (602) (ΔCD, ΔSWA, ΔRH) using a difference between the baseline pattern signal ($I_{BP}$) and the perturbed pattern signal ($I_{PP}$). As an additional input there may be used a known influence (604) (∂P/∂CD, ∂P/∂SWA, ∂P/∂RH) of the pattern signal on one or more of the pattern profile parameters (CD, SWA, RH). In this example, only the gradient of the pupil image signal, P is used. However, in other embodiments the Hessian term of the Taylor expansion may be used. Embodiments of the present invention are therefore not limited to the first derivative only.

Also used in the calculation is a difference (606) (Δstack) between the baseline stack signal ($I_{BS}$) and the perturbed stack signal ($I_{PS}$). In this embodiment this step includes, for the stack calculation, calculating (608) values of differential stack parameters (610) ($\Delta H_i$, $\Delta n_i$, $\Delta k_i$) using the difference (606) between the baseline stack signal ($I_{BS}$) and the perturbed stack signal ($I_{PS}$) and dependence (612) of a stack signal on stack parameters (∂P/∂H, ∂P/∂n, ∂P/∂k) and feeding forward these calculated values of differential stack parameters (610) ($\Delta H_i$, $\Delta n_i$, $\Delta k_i$) to the calculation (600) of values of differential pattern profile parameters (602) (ΔCD, ΔSWA, ΔRH).

The line/space calculation step for calculating (600) values of differential pattern profile parameters (602) (ΔCD, ΔSWA, ΔRH) may be performed using a Bayesian differential cost function, as described below. The stack calculation step (608) may also use a Bayesian differential cost function.

The fed-forward calculated values of differential stack parameters (610) ($\Delta H_i$, $\Delta n_i$, $\Delta k_i$) may be kept constant in the line/space calculation step 600).

The a posterior probability density function (PDF) of the profile parameters, p, can be computed from Bayes theorem as follows:

$$f(\underline{p}|\underline{I}_{measured}) = \frac{f_{likelihood}(\underline{I}_{measured}|\underline{p}) \cdot f_{prior}(\underline{p})}{f_{normalizing}(\underline{I}_{measured})}$$

Where $f_{posterior}(\underline{p}|\underline{I}_{measured})$ denotes the a posteriori conditional probability density function of the parameters $\underline{p}$, given the occurrence of the measured intensities $\underline{I}_{measured}$.

Where $f_{likelihood}(\underline{I}_{measured}|\underline{p})$ denotes the likelihood conditional probability density function of the measured intensities $\underline{I}_{measured}$, given the occurrence of the parameters $\underline{p}$.

Where $f_{normalizing}(\underline{I}_{measured})$ denotes the probability density function of the measured intensities $\underline{I}_{measured}$.

Statistically we will assume that a priori we know that $\underline{p}$ is a random variable with a normal multivariate distribution, with expected values $\underline{\mu}_{prior}$ and with covariance $\underline{C}_{prior}$.

The prior normal multivariate probability density function is defined to be:

$$f_{prior}(\underline{p}) = \frac{1}{\sqrt{\det(2\pi \cdot \underline{C}_{\underline{p},prior})}} \cdot \exp\left[-\frac{1}{2} \cdot (\underline{p} - \underline{\mu}_{\underline{p},prior})^T \cdot \underline{C}_{\underline{p},prior}^{-1} \cdot (\underline{p} - \underline{\mu}_{\underline{p},prior})\right]$$

The likelihood normal multivariate probability density function is defined to be:

$$f_{likelihood}(I_{measure} \mid \underline{p}) = \frac{1}{\sqrt{\det(2\pi \cdot \underline{C}_I)}} \cdot$$

$$\exp\left[-\frac{1}{2} \cdot (I_{measured} - I_{model}(\underline{p}))^T \cdot \underline{C}_I^{-1} \cdot (I_{measured} - I_{model}(\underline{p}))\right]$$

Where $\underline{C}_I$ denotes the covariance matrix of the measured intensities.

For measuring delta profile measurement, there are two measured pupils and two measured profile parameters. The two measured pupils are the baseline pupil, $I_{baseline}$, and the perturbed pupil, $I_{perturbed}$. The profile parameters corresponding to these two pupils are b for the baseline pupil and p for the perturbed pupil. We are interested in measuring the difference between the two profiles where u=p−b. b is a vector variable for the baseline pupil, while p is a vector variable for the perturbed pupil. The vector variable b and p are composed of CD, SWA, RH for the baseline pupil and perturbed pupil respectively. H, n and k are in the vector variables, b and p, for the baseline and perturbed pupils. The Bayesian method in this example is used twice. First the Bayesian method is used to determine u of the thin-film parameters H, n and k. Where p=b+u. u is delta(H), delta(n), delta(k). After $u_{thin-film}$ is determined, it is fed forward to the second Bayesian reconstruction of CD, SWA, and RH. And u of the pattern is then calculated where u of the pattern is delta(CD), delta(SWA) and delta(RH). So there are $\{u_{thin-film}, b_{thin-film}, p_{thin-film}\}$ and $\{u_{pattern}, b_{pattern}, p_{pattern}\}$.

And the PDF for the difference, u, with the measured data, $I_{measured}$, is shown below in which Bayes theorem was applied:

$$f(u \mid I_{measured}) = \frac{f_{likelihood}(I_{perturbed} \mid \underline{p}) \cdot f_{prior}(\underline{p})}{f_{normalizing}(I_{perturbed})} -$$

$$\frac{f_{likelihood}(I_{baseline} \mid \underline{b}) \cdot f_{prior}(\underline{b})}{f_{normalizing}(I_{baseline})}$$

$$= \frac{f_{likelihood}(I_{perturbed} \mid \underline{u} + \underline{b}) \cdot f_{prior}(\underline{u} + \underline{b})}{f_{normalizing}(I_{perturbed})} -$$

$$\frac{f_{likelihood}(I_{baseline} \mid \underline{b}) \cdot f_{prior}(\underline{b})}{f_{normalizing}(I_{baseline})}$$

Taking the natural log of the equation above:

$\ln[f(\underline{u}|I_{measured})] = \ln[f_{likelihood}(I_{perturbed}|\underline{u}+\underline{b})] + \ln[f_{prior}(\underline{u}+\underline{b})] - \ln[f_{normalizing}(I_{perturbed})] - \ln[f_{likelihood}(I_{baseline}|\underline{b})] - \ln[f_{prior}(\underline{b})] + \ln[f_{normalizing}(I_{baseline})]$ If we assume that the same scatterometer tool is used to measure the perturbed wafer and the baseline wafer and the scatterometer tool is not changing over time, we make the following assumption about the PDF:

$$f_{normalizing}(I_{perturbed}) = f_{normalizing}(I_{baseline})$$

And the equation above simplifies to:

$\ln[f(\underline{u}|I_{measured})] = \ln[f_{likelihood}(I_{perturbed}|\underline{u}+\underline{b})] + \ln[f_{prior}(\underline{u}+\underline{b})] - \ln[f_{likelihood}(I_{baseline}|\underline{b})] - \ln[f_{prior}(\underline{b})]$ We wish to maximize the posterior solution to u by calculating the maximum likelihood estimate of u (MLE of u). To find the MLE of u, four PDF's are needed; two for the baseline pupils and two for the perturbed pupils. The two baseline PDF's are:

$$f_{prior}(\underline{b}) = \frac{1}{\sqrt{\det(2\pi \cdot \underline{C}_{b,prior})}} \cdot \exp\left[-\frac{1}{2} \cdot (\underline{b} - \underline{\mu}_{b,prior})^T \cdot \underline{C}_{b,prior}^{-1} \cdot (\underline{b} - \underline{\mu}_{b,prior})\right]$$

$$f_{likelihood}(I_{baseline} \mid \underline{b}) = \frac{1}{\sqrt{\det(2\pi \cdot \underline{C}_I)}} \cdot$$

$$\exp\left[-\frac{1}{2} \cdot (I_{baseline} - I_{model}(\underline{b}))^T \cdot \underline{C}_{I_{baseline}}^{-1} \cdot (I_{baseline} - I_{model}(\underline{b}))\right]$$

The two perturbed PDFs are:

$$f_{prior}(\underline{u} + \underline{b}) = \frac{1}{\sqrt{\det(2\pi \cdot \underline{C}_{p,prior})}} \cdot$$

$$\exp\left[-\frac{1}{2} \cdot (\underline{u} + \underline{b} - \underline{\mu}_{p,prior})^T \cdot \underline{C}_{p,prior}^{-1} \cdot (\underline{u} + \underline{b} - \underline{\mu}_{p,prior})\right]$$

$$f_{likelihood}(I_{perturbed} \mid \underline{u} + \underline{b}) = \frac{1}{\sqrt{\det(2\pi \cdot \underline{C}_{I_{perturbed}})}} \cdot \exp\left[-\frac{1}{2} \cdot\right.$$

$$\left.(I_{perturbed} - I_{model}(\underline{u} + \underline{b}))^T \cdot \underline{C}_{I_{perturbed}}^{-1} \cdot (I_{perturbed} - I_{model}(\underline{u} + \underline{b}))\right]$$

Before substituting the PDF's into the MLE of u equation above, there are four assumptions that may be made. The first two assumptions are good assumptions, the third assumption has been tested and proven to be valid.

List of Assumptions:

1. The expected values of $\underline{b}$ and $\underline{p}$ ($\underline{\mu}_b$ and $\underline{\mu}_p$) are equivalent since we assume small changes, i.e., $\underline{u}$ is small.

2. The covariance of $\underline{b}$ and $\underline{p}$ ($C_{b,prior}$ and $C_{p,prior}$) are equivalent since we assume u to nor, be small. For this work we can for example use a diagonal matrix equivalent to the assumption $\underline{C}_{p,prior} = \underline{C}_{b,prior} = \text{diag}(\sigma_{b,prior}^2)$. It is important to note that the matrix is not truly diagonal. For example, when the pattern is printed out of focus, the resist thickness decreases, the sidewall increases and depending on the curvature of the Bossung the CD decreases. Using forward simulations, a better estimate of the covariance matrix can be made.

3. The perturbed model pupil, $I_{model}(\underline{u}+\underline{b})$, can be calculated through a Taylor series expansion as:

$$I_{model}(\underline{u} + \underline{b}) = I_{model}(\underline{b}) + \underline{u} \cdot \nabla_{\underline{b}} I_{model}(\underline{b}) + \underline{u}^T \cdot \nabla_{\underline{b}} \nabla_{\underline{b}'} I_{model}(\underline{b}) \cdot \underline{u} + \ldots \approx$$

$$I_{model}(\underline{b}) + \underline{u} \cdot \nabla_{\underline{b}} I_{model}(\underline{b})$$

4. Assumption 3 above assumes that the Jacobian of $I_{model}(\underline{b})$ only needs to be calculated using the baseline profile parameters, $\underline{b}$. It assumes that the Jacobian does not need to be updated as $\underline{u}$ changes. Allowing the Jacobian to be updated is possible if the assumption is poor. However, this would increase the computational time. With these assumptions the cost function for the MLE of $\underline{u}$ can be written as $$\ln[f(\underline{u}\mid \underline{I}_{measured})] = -\frac{1}{2}\ln\left[\det\left(2\pi\cdot\underline{\underline{C}}_{\underline{I}_{perturbed}}\right)\right] -$$

$$\frac{1}{2}\cdot\left(\underline{I}_{perturbed} - \underline{I}_{model}(\underline{b}) - \underline{u}\cdot\nabla_{\underline{b}}\underline{I}_{model}(\underline{b})\right)^T \cdot \underline{\underline{C}}^{-1}_{\underline{I}_{perturbed}} \cdot$$

$$\left(\underline{I}_{perturbed} - \underline{I}_{model}(\underline{b}) - \underline{u}\cdot\nabla_{\underline{b}}\underline{I}_{model}(\underline{b})\right) - \frac{1}{2}\ln\left[\det\left(2\pi\cdot\underline{\underline{C}}_{\underline{b},prior}\right)\right] -$$

$$\frac{1}{2}\cdot\left(\underline{u}+\underline{b}-\underline{\mu}_{\underline{b},prior}\right)^T \cdot \underline{\underline{C}}^{-1}_{\underline{b},prior} \cdot \left(\underline{u}+\underline{b}-\underline{\mu}_{\underline{b},prior}\right) +$$

$$\frac{1}{2}\ln\left(\det\left(2\pi\cdot\underline{\underline{C}}_{\underline{I}_{baseline}}\right)\right) +$$

$$\frac{1}{2}\cdot\left(\underline{I}_{baseline} - \underline{I}_{model}(\underline{b})\right)^T \cdot \underline{\underline{C}}^{-1}_{\underline{I}_{baseline}} \cdot \left(\underline{I}_{baseline} - \underline{I}_{model}(\underline{b})\right) +$$

$$\frac{1}{2}\ln\left[\det\left(2\pi\cdot\underline{\underline{C}}_{\underline{b},prior}\right)\right] + \frac{1}{2}\cdot\left(\underline{b}-\underline{\mu}_{\underline{b},prior}\right)^T \cdot \underline{\underline{C}}^{-1}_{\underline{b},prior} \cdot \left(\underline{b}-\underline{\mu}_{\underline{b},prior}\right)$$

There are two covariance matrices of the measured pupils that are needed to further simplify the equation above. The measured covariance matrices are for example given by:

$$\underline{\underline{C}}_{\underline{I}_{baseline}} = \mathrm{diag}(\alpha^2 \underline{I}_{baseline} + \varepsilon^2)$$

$$\underline{\underline{C}}_{\underline{I}_{perturbed}} = \mathrm{diag}(\alpha^2 \underline{I}_{perturbed} + \varepsilon^2)$$

These are example covariance matrices on the measured intensities. There are others that could be used. Embodiments of the present invention are not limited to only this model. In these matrices the $\alpha^2 I$ term is from shot noise of the scatterometer sensor, and $\varepsilon^2$ is from the dark current of the scatterometer sensor. The determinant of $$\underline{\underline{C}}^{-1}_{\underline{I}_{baseline}} \text{ is: } \det\left(2\pi\cdot\underline{\underline{C}}_{\underline{I}_{baseline}}\right) = 2\pi\prod_i(\alpha^2 I_{i,baseline} + \varepsilon^2)$$

where i is the index of the pupil pixel location. The inverse of $\underline{\underline{C}}_{\underline{I}_{baseline}}$ is:

$$\underline{\underline{C}}^{-1}_{\underline{I}_{baseline}} = \mathrm{diag}\left(\frac{1}{\alpha^2 I_{baseline} + \varepsilon^2}\right)$$

If we define the difference between the two measured pupils, $\underline{I}_{baseline}$ and $\underline{I}_{perturbed}$, to be: $\underline{I}_u = \underline{I}_{perturbed} - \underline{I}_{baseline}$ the covariance of $\underline{I}_{perturbed}$ can be written as shown below:

$$\underline{\underline{C}}_{\underline{I}_{perturbed}} =$$

$$\mathrm{diag}(\alpha^2(I_u + I_{baseline}) + \varepsilon^2) = \mathrm{diag}\left[(\alpha^2 I_{baseline} + \varepsilon^2)\left(1 + \frac{\alpha^2 I_u}{\alpha^2 I_{baseline} + \varepsilon^2}\right)\right]$$

Both the determinant and inverse of $\underline{\underline{C}}_{\underline{I}_{perturbed}}$ is needed. The determinant is given by:

$$\det(2\pi\cdot\underline{\underline{C}}_{\underline{I}_{perturbed}}) = 2\pi\prod_i(\alpha^2 I_{i,baseline} + \alpha^2 I_{i,u} + \varepsilon^2)$$

Then $$-\frac{1}{2}\ln\left[\det\left(2\pi\cdot\underline{\underline{C}}_{\underline{I}_{perturbed}}\right)\right] + \frac{1}{2}\ln\left[\det\left(2\pi\cdot\underline{\underline{C}}_{\underline{I}_{baseline}}\right)\right]$$

$$= -\frac{1}{2}\sum_i \frac{\alpha^2 I_u}{\alpha^2 I_{i,baseline} + \varepsilon^2}$$

in which $\ln(1+x)\approx x$ was used for small x.

The inverse is given by:

$$\underline{\underline{C}}^{-1}_{\underline{I}_{perturbed}} = \mathrm{diag}\left[\frac{1}{\alpha^2 I_{baseline} + \varepsilon^2} \cdot \frac{1}{1 + \frac{\alpha^2 I_u}{\alpha^2 I_{baseline} + \varepsilon^2}}\right]$$

$$\approx \mathrm{diag}\left[\frac{1}{\alpha^2 I_{baseline} + \varepsilon^2} \cdot \left(1 - \frac{\alpha^2 I_u}{\alpha^2 I_{baseline} + \varepsilon^2}\right)\right]$$

$$= \mathrm{diag}\left[\frac{1}{\alpha^2 I_{baseline} + \varepsilon^2}\right] - \mathrm{diag}\left[\frac{\alpha^2 I_u}{(\alpha^2 I_{baseline} + \varepsilon^2)^2}\right]$$

$$\approx \mathrm{diag}\left[\frac{1}{\alpha^2 I_{baseline} + \varepsilon^2}\right]$$

$$= \underline{\underline{C}}^{-1}_{\underline{I}_{baseline}}$$

Substituting these equations into the MLE of u:

$$\ln[f(\underline{u}\mid \underline{I}_{measured})] = -\frac{1}{2}\sum_i \frac{\alpha^2 I_u}{\alpha^2 I_{i,baseline} + \varepsilon^2} -$$

$$\frac{1}{2}\cdot\underline{u}^T\cdot\underline{\underline{C}}^{-1}_{\underline{b},prior}\cdot\underline{u} - \frac{1}{2}\cdot\left(\underline{I}_{perturbed} - \underline{I}_{baseline} - \underline{u}\cdot\nabla_{\underline{b}}\underline{I}_{model}(\underline{b})\right)^T \cdot$$

$$\underline{\underline{C}}^{-1}_{\underline{I}_{baseline}} \cdot \left(\underline{I}_{perturbed} - \underline{I}_{baseline} - \underline{u}\cdot\nabla_{\underline{b}}\underline{I}_{model}(\underline{b})\right)$$

Since we wish to maximize the likelihood above, the first term is dropped since its derivative with respect to u is zero. The MLE above needs to be maximized with respect to u. In the current method, the cost function is minimized. This is accomplished by multiplying the above equation by $-1$.

$$\ln[f(\underline{u}\mid \underline{I}_{measured})] =$$

$$\frac{1}{2}\cdot\underline{u}^T\cdot\underline{\underline{C}}^{-1}_{\underline{b},prior}\cdot\underline{u} + \frac{1}{2}\cdot\left(\underline{I}_{perturbed} - \underline{I}_{baseline} - \underline{u}\cdot\nabla_{\underline{b}}\underline{I}_{model}(\underline{b})\right)^T \cdot$$

$$\underline{\underline{C}}^{-1}_{\underline{I}_{baseline}} \cdot \left(\underline{I}_{perturbed} - \underline{I}_{baseline} - \underline{u}\cdot\nabla_{\underline{b}}\underline{I}_{model}(\underline{b})\right) =$$

$$\frac{1}{2}\cdot\|\underline{I}_{perturbed} - \underline{I}_{baseline} - \underline{u}\cdot\nabla_{\underline{b}}\underline{I}_{model}(\underline{b})\|^2_{\underline{\underline{C}}^{-1}_{\underline{I}_{baseline}}} + \frac{1}{2}\|\underline{u}\|^2_{\underline{\underline{C}}^{-1}_{\underline{b},prior}}$$

The MLE above can be rewritten into the following weighted least squares problem:

$$\begin{cases} \underline{u}_{map} = \mathrm{argmin}\{\ln[f(\underline{u}\mid \underline{I}_{measured})]\} = \mathrm{argmin}\left(\frac{1}{2}\cdot\|R'(\underline{u})\|^2_2\right) \\ R'(\underline{u}) = \begin{bmatrix} \underline{\underline{C}}^{-1/2}_{\underline{I}_{baseline}} \cdot \left(\underline{I}_{perturbed} - \underline{I}_{baseline} - \underline{u}\cdot\nabla_{\underline{b}}\underline{I}_{model}(\underline{b})\right) \\ \underline{\underline{C}}^{-1/2}_{\underline{b},prior}\cdot\underline{u} \end{bmatrix} \end{cases}$$

The Jacobian matrix of this weighted least squares minimization problem equals $$\underline{\underline{J}}'(\underline{u}) = \frac{\partial \underline{R}'(\underline{u})}{\partial \underline{u}}$$

$$= \frac{\partial}{\partial \underline{u}} \begin{bmatrix} \underline{\underline{C}}_{I_{baseline}}^{-1/2} \cdot (I_{perturbed} - I_{baseline} - \underline{u} \cdot \nabla_{\underline{b}} I_{model}(\underline{b})) \\ \underline{\underline{C}}_{\underline{b},prior}^{-1/2} \cdot \underline{u} \end{bmatrix}$$

$$= \begin{bmatrix} -\underline{\underline{C}}_{I_{baseline}}^{-1/2} \cdot \nabla_{\underline{b}} I_{model}(\underline{b}) \\ \underline{\underline{C}}_{\underline{b},prior}^{-1/2} \end{bmatrix}$$

$$= \begin{bmatrix} -\underline{\underline{C}}_{I_{baseline}}^{-1/2} \cdot \underline{\underline{J}}_{model}(\underline{b}) \\ \underline{\underline{C}}_{\underline{b},prior}^{-1/2} \end{bmatrix}$$

The differential cost function proposed above may be referred to as BDIF (Bayesian Differential).

$$\underline{u}_{BDIF} = \operatorname{argmin} \begin{bmatrix} \frac{1}{2} \cdot (I_{perturbed} - I_{baseline} - \underline{u} \cdot \nabla_{\underline{b}} I_{model}(\underline{b}))^T \cdot \\ \underline{\underline{C}}_{I_{baseline}}^{-1} \cdot (I_{perturbed} - I_{baseline} - \underline{u} \cdot \nabla_{\underline{b}} I_{model}(\underline{b})) + \\ \frac{1}{2} \cdot \underline{u}^T \cdot \underline{\underline{C}}_{\underline{b},prior}^{-1} \cdot \underline{u} \end{bmatrix}$$

In BDIF, a regularization term, $\underline{u}^T \cdot \underline{\underline{C}}_{\underline{b},prior}^{-1} \cdot \underline{u}$, appears. Consequently, the matrix should be well-conditioned. Since the expected value of $\underline{u}$ is the zero vector, one does not have to provide an expected value of the difference. Also, this method can be used sequentially as described with reference to FIG. 6. First $\underline{u}_{thin-film}$ the difference in the thin-film stack parameters, n, k and thickness, can be determined by comparing unexposed regions on the two wafers, baseline wafer and perturbed wafer. The thin-film stack differences can be fed forward to the CD measurement, and in the second sequence only the profile parameters, $\underline{u}_{CD}$, are allowed to change while keeping the thin-film stack differences, $\underline{u}_{thin-film}$, constant. Optimally $\underline{u}_{BDIF} = [\underline{u}_{thin-film} \underline{u}_{CD}]^T$.

As discussed in assumption 4, the gradient of $I_{model}$ is only calculated once based on the baseline parameters, $\underline{b}$. However, the gradient of $I_{model}$ may have to be updated. If gradient needs to be updated, $\underline{u}_{BDIF}$ becomes the equation below. This results in better accuracy in calculation of the parameter difference, $\underline{u}$, but it will increase the computation time.

$$\underline{u}_{BDIF} = \operatorname{argmin} \begin{bmatrix} \frac{1}{2} \cdot (I_{perturbed} - I_{baseline} - \underline{u} \cdot \nabla_{\underline{u}+\underline{b}} I_{model}(\underline{u}+\underline{b}))^T \cdot \\ \underline{\underline{C}}_{I_{baseline}}^{-1} \cdot (I_{perturbed} - I_{baseline} - \underline{u} \cdot \nabla_{\underline{u}+\underline{b}} I_{model}(\underline{u}+\underline{b})) + \\ \frac{1}{2} \cdot \underline{u}^T \cdot \underline{\underline{C}}_{\underline{b},prior}^{-1} \cdot \underline{u} \end{bmatrix}$$

Appendix:

$$f(b) = e^{-b^2}$$

$$f(u+b) = e^{-(u+b)^2} = e^{-u^2 - 2ub - b^2}$$

Using the fact that exp(x) for small x equals 1+x below $$\ln[f(b) - f(u+b)] = \ln[e^{-b^2} - e^{-u^2 - 2ub - b^2}]$$
$$= \ln[e^{-b^2} - e^{-u^2 - 2ub} e^{-b^2}]$$
$$= \ln[e^{-b^2}(1 - e^{-u^2 - 2ub})]$$
$$\approx \ln[e^{-b^2}(1 - (1 - u^2 - 2ub))]$$
$$= \ln[e^{-b^2} \cdot (u^2 + 2ub)]$$
$$= -b^2 + \ln(u^2 + 2ub)$$

$$\ln[f(b)] - \ln[f(u+b)] = \ln(e^{-b^2}) - \ln(e^{-u^2 - 2ub - b^2})$$
$$= u^2 + 2ub$$

Taking the derivatives $$\frac{\partial \ln[f(b) - f(u+b)]}{\partial u} = \frac{u+b}{\frac{1}{2}u^2 + ub}$$

$$\frac{\partial \{\ln[f(b)] - \ln[f(u+b)]\}}{\partial u} = 2u + 2b$$

Comparing the derivatives for small u $$\frac{\partial \ln[f(b) - f(u+b)]}{\partial u} > \frac{\partial \{\ln[f(b)] - \ln[f(u+b)]\}}{\partial u}$$

So $$\frac{\partial \{\ln[f(b)] - \ln[f(u+b)]\}}{\partial u}$$

is lower bound on $$\frac{\partial \ln[f(b) - f(u+b)]}{\partial u}.$$

Since we are maximizing with respect to u, we can use the lower bound $$\frac{\partial \{\ln[f(b)] - \ln[f(u+b)]\}}{\partial u}.$$

Figure 7:
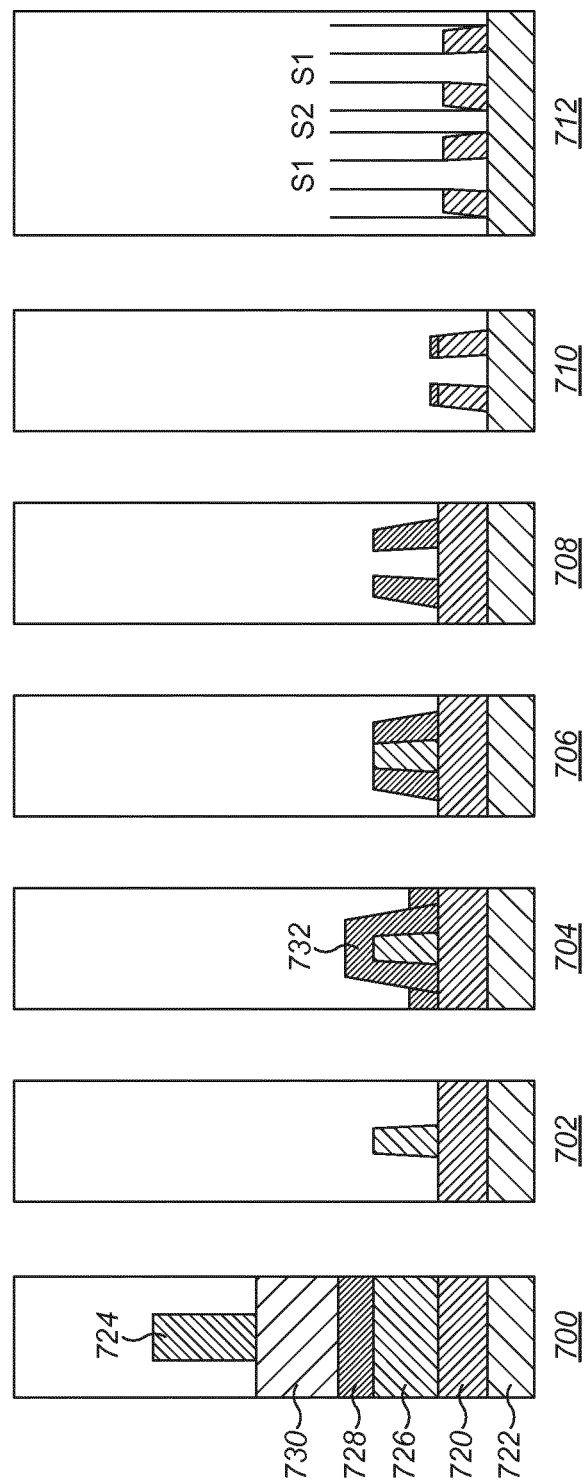
FIG. 7 illustrates a process of producing product features by double patterning, for illustrating the application of a second embodiment of the invention.

We turn now to the second example illustrating the use of differences between pattern signals, for example scatterometry pupil images. As background, FIG. 7 illustrates a so-called double patterning process performed on a substrate. Spacer Process Technology is one such process for achieving product patterns of high resolution with existing lithography tools. It is described for example in the paper "Double patterning for 32 nm and below: an update", by J. Finders et. al., Proc. SPIE 6924, 692408 (2008) (http://dx.doi.org/10.1117/12.772780). The method is performed in steps illustrated schematically and numbered 700-712. A device pattern comprising for example an array of fine lines is to be produced in a material layer 720 on substrate 722. The material layer 720 may be a polysilicon layer on top of gate oxide layer (too thin to be seen in the drawing) for example on a silicon substrate. In a lithography step 700, a line pattern having half the pitch of the desired device pattern has been formed in a resist layer 724. For the purpose of the lithographic process, additional layers are provided between the resist and the oxide layer 720. These are amorphous carbon (a-C) hard mask layer 726, a SiOC or nitride layer 728 and an antireflection coating (BARC) 730.

Using the line or resist printed in the lithography step, a line is etched (702) into the hard mask, covered (704) with a spacer material 732, and etched again (706). In a further etch (708) the hard mask material is removed. A line doubling results, and the remaining spacer material can be used as a mask to etch (710) a pair of thinner lines into the polysilicon material layer 720. At 712 we see part of a larger pattern where pairs of lines are formed side by side to form an array of fine lines. These lines, which are the subject of our measurement method example, may be functional device features, for example in a memory product. They may also be a grating dedicated to the measurement function, but representing device features elsewhere on the same substrate.

Figure 8:
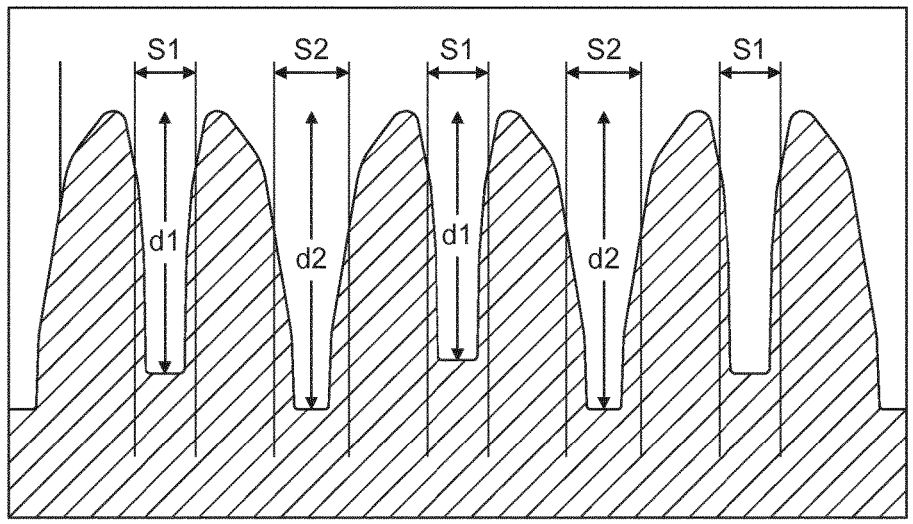
FIG. 8 illustrates certain parameters of a pattern target in the second embodiment.

Referring also to the enlarged profile shown in FIG. 8, various dimensions of the formed lines are defined. Each line has parameters such as CD, SWA and H, but these are not all identical, due to the way they have been formed by the doubling process. The space S1 in between the lines from one line pair is the remnant of the resist line formed in the lithographic process. The space in between adjacent line pairs, S2, is the resultant of the pitch of the lines printed in the resist layer, minus S1 and the two line CD's. It is important to control the balance between S1 and S2, since an imbalance will result in an effective overlay error between the odd and the even lines. For techniques to measure the S1–S2 imbalance after final etch, the state of the art is described by P. Dasari et. al. in "Metrology characterization of spacer double patterning by scatterometry", Proc. SPIE 7971, 797111 (2011) (http://dx.doi.org/10.1117/12.879900).

A first known technique is to measure the profile directly with CD-SEM (scanning electron microscopy). A cross sectional image similar to FIG. 8 can be obtained and features measured directly from the image. Unfortunately, each CD-SEM measurement is time-consuming and also it can be difficult to discriminate between the spaces S1 and S2.

A second known technique is to measure with scatterometry, using instruments of the type shown in FIGS. 3 and 4.

Figure 9:
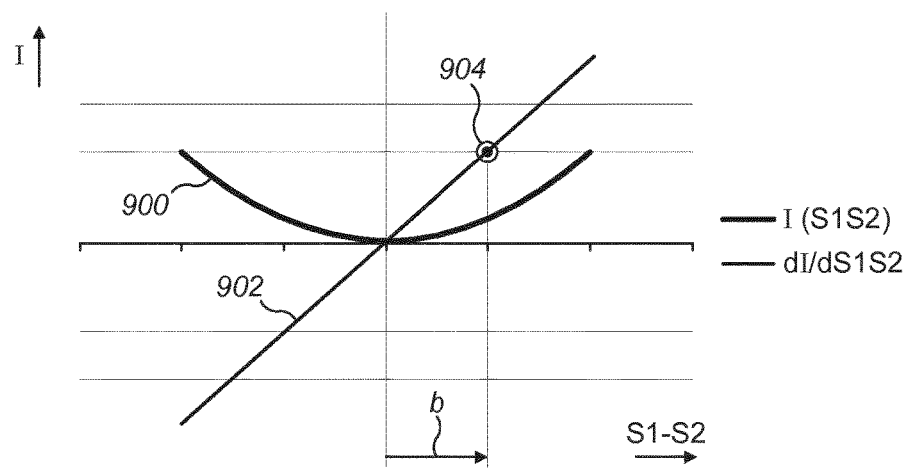
FIG. 9 illustrates the sensitivity of part of a pattern signal in the second embodiment.

The parameters CD, S1, S2 etc. can be reconstructed by calculations using the pattern signals (pupil image intensities or the like) obtained from the target. A first problem with this approach is that the sensitivity of the scatterometry to S1–S2 imbalance diminishes to zero, in the case of zero imbalance (S1=S2), due to the symmetry obtained in such a situation. In FIG. 9 the bold curve 900 represents the dependence of a scatterometry signal I against the imbalance, represented by S1–S2. Also shown as curve 902 is a derivative of the signal. The scales are arbitrary. In the region of zero imbalance, the derivative is zero, and sensitivity is zero as a result.

The symmetry can be broken, and the sensitivity restored, in two ways. A first way is if the processing has a remaining asymmetry, for instance an imbalance between the etch depth d1 in space S1 and the etch depth d2 in space S2, as shown in FIG. 8. The processing, however, will be optimized to reduce these kinds of asymmetry after final etch. Therefore this measurement method becomes less useful as product quality improves. The second approach is to use a dedicated metrology target, in which a deliberate bias b is introduced in the S1–S2 value. The signal moves away from the point of zero sensitivity to a point 904 on the curve where the derivative is substantial. A problem with this approach is that the metrology targets occupy space, and may in practice be relatively large, for example 40 µm square to avoid interference from neighboring features. The sensitivity of the measurement is in any even weak and prone to cross-talk from other process variations.

The above described principle of calculating differential profile parameters directly from the scatterometry signals of two targets allows more accurate and/or more convenient measurement of difficult parameters such as spacing imbalance in doubled patterns. The second example method now described is based upon the property that the scatterometry signal, as seen in FIG. 9 is an even function of (S1–S2). The sensitivity (derivative of the raw signal towards (S1–S2) is therefore an odd function of (S1–S2). By application of a bias, a sensitivity can be created, the sign being dependent on the sign of the bias (see figure below). A new target design is created, in combination with a scatterometry based metrology method.

Figure 10:
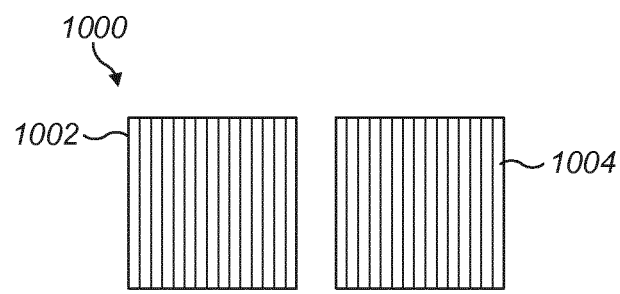
FIG. 10 illustrates a composite metrology target used in the second embodiment.
Figure 11:
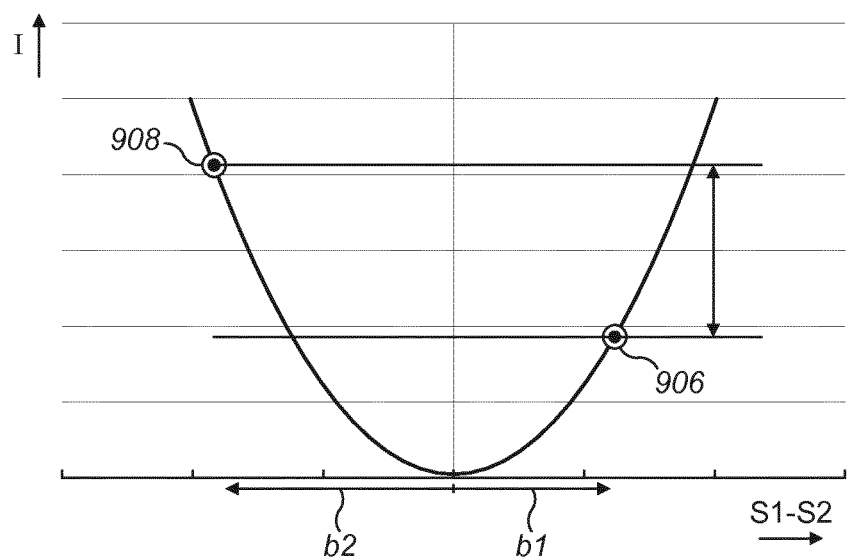
FIG. 11 illustrates the pattern signals for a biased pair of targets.

FIG. 10 illustrates schematically a new target 1000 which is a combination of at least two sub-targets 1002, 1004. The features in the targets are line/space patterns formed with the full SPT process, as shown in FIG. 7. As with other metrology targets, separate targets may be made for X- and Y-oriented lines (not shown). FIG. 11 illustrates the dependency of the scatterometry signals I in an example where the sub-targets are both formed with biased features, but having a different bias values for S1–S2, labeled b1 and b2. The bias is opposite. In this way, the difference in signals obtained from the two targets is—in first approximation—a linear function of the average value of (S1–S2).

The targets are measured by scatterometry and a differential profile parameter representing the S1–S2 imbalance is calculated using an adaptation of the method described already with respect to FIG. 6. Specifically, the raw signals obtained by the scatterometer are subtracted to get a difference signal, and the difference signal is used, together with knowledge of the biases and other model parameters, to determine to the average value of imbalance (S1–S2) over the targets. This is a measure for the variation in S1–S2 of the (unbiased) product lines and spaces. Since in this example the sub-targets are formed side-by-side in the same process, there is no need for the steps 606, 608 to measure and subtract corrections to compensate differences in the underlying stack. Also, since the difference in the scattered radiation is, in first order approximation, only a function of (S1–S2), the full scatterometry signal can be used to determine S1–S2. (There is no need to reconstruct other parameters of the structure.) The target design may be optimized to reduce the influence of other parameters and process variables, so as to improve the accuracy of this approximation.

Using the full reflectance to determine the parameter (S1–S2) can bring one or more of the following advantages. Improved precision can be obtained. A factor of five improvement has been obtained in a real example by moving from full reconstruction of one biased target to using the difference of signals from oppositely biased differential targets. The target size can be reduced and even be smaller than the measurement spot. Instead of measuring intensities in the pupil plane of the scatterometer, changes can be measured in the object plane, using an imaging branch of the known scatterometer (not shown in FIGS. 3 and 4). Such techniques for performing scatterometry on small targets are known in principle from published patent applications such as US 2010328655 and US2011043791A1, the contents of which are incorporated herein by reference. The parameter of interest in those disclosures is typically overlay between patterns formed on top of one another, but the process can be adapted readily to measure asymmetry caused by other effects, such as space imbalance in a double patterning process. The composite target 1000 may in particular be small enough that radiation diffracted by both sub-targets 1002 and 1004 can be captured in a single image. By selecting the corresponding areas of the image, the intensity difference can be determined.

The skilled reader can readily envisage modifications of the above examples, both to measure the same differential profile parameters as discussed above, and/or to measure other parameters for process or imaging monitoring purposes.

All that is required is to design a differential target pair, where the difference in reflection in at least a certain part of the raw scattered radiation signal is, in first order approximation, proportional only to the value of a single parameter of interest. In each application, a differential profile parameter representing a difference between two targets can be calculated without the intermediate step of calculating absolute parameter for each target. Depending on the context, the targets and their profiles may conveniently be referred to as "baseline" vs "perturbed", or "reference" vs "subject", without limiting the generality of the underlying technique.

Depending on the application, the substrate with the first pattern target may be the same as or different from the substrate with the second pattern target. In the first example described above, the targets may be on different substrates, while the differential profile parameters may be used to reveal a difference between processes executed on different apparatus, and/or processes executed at different times. Where the first pattern target and the second pattern target are both on the same substrate, the differential profile parameters may be used to reveal a difference between processes executed at different locations on the same substrate or within a portion of the substrate. Stack targets may be measured in this case, if it is deemed necessary to compensate for variation of parameters of the underlying stack. Alternatively, as in the second example described above, the first pattern target and second pattern targets may be a pair of differently biased sub-targets, formed by a common process at substantially the same position on the same substrate. Differently biased sub-targets in this context means two or more targets designed so that their profile parameters have different sensitivities to a parameter of interest in a process by which they are performed. In principle, the sub-targets could be one which is unbiased. A sub-target pair could include one which is not sensitive to the parameter of interest and one (biased or not biased) which is.

Another example showing different parameters that can be measured is for the monitoring of lens aberrations. For this, differential targets have been developed where the CD difference is a function of the lens aberration. Application of the differential measurement technique, according to the invention as described above, will have similar merits in terms of improved precision, and optionally reduced target size.

When referring to the "difference" between signals, it should be understood that this encompasses a ratiometric (percentage) difference, not only a different obtained by subtraction. The skilled person can choose the correct comparison technique, and the most appropriate manner of representing differences.

Although specific reference may be made in this text to the use of inspection methods and apparatus in the manufacture of ICs, it should be understood that the inspection methods and apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection method, comprising:
   illuminating a first pattern target having first profile parameters with radiation and detecting scattered radiation to obtain a first pattern signal;
   illuminating a second pattern target having second profile parameters, the second pattern target different than the first pattern target, with radiation and detecting scattered radiation to obtain a second pattern signal; and
   calculating values of differential pattern profile parameters using a difference between the first pattern signal and the second pattern signal,
   wherein the differential pattern profile parameters are differences between the first and second profile parameters, and
   wherein the calculating comprises using predetermined information, the predetermined information comprising a first or a higher order derivative of the first pattern signal with respect to one of the first profile parameters.

2. The method of claim 1, wherein the calculating further comprises calculating the values of the differential pattern profile parameters using a regularized cost function.

3. The method of claim 2, wherein the cost function is a Bayesian differential cost function.

4. The method of claim 1, further comprising:
   illuminating a first stack target with radiation and detecting scattered radiation to obtain a first stack signal; and
   illuminating a second stack target with radiation and detecting scattered radiation to obtain a second stack signal,
   wherein the calculating comprises using a difference between the first stack signal and the second stack signal, thereby to reduce an influence of variations between stacks underlying the first and second pattern targets.

5. The method of claim 4, wherein the calculating further comprises:
   calculating values of differential stack parameters using the difference between the first stack signal and the second stack signal and predetermined information as to the dependence of at least one of the first and second stack signals on stack parameters; and
   using the calculated values of differential stack parameters, in the calculating values of differential pattern profile parameters.

6. The method of claim 5, wherein the calculating values of differential stack parameters uses a Bayesian differential cost function.

7. The method of claim 5, wherein the calculated values of differential stack parameters are kept constant when calculating values of differential pattern profile parameters.

8. An inspection apparatus, comprising:
   an optical system configured to illuminate one or more pattern targets with radiation and detect scattered radiation to obtain a corresponding pattern signal; and
   a processor configured to calculate values of differential pattern profile parameters using a difference between a first pattern signal detected from a first pattern target having first profile parameters using the optical system and a second pattern signal detected from a second pattern target, different than the first pattern target and having second profile parameters, using the optical system,
   wherein the differential pattern profile parameters are differences between the first and second profile parameters, and
   wherein the calculating comprises using predetermined information, the predetermined information comprising a first or a higher order derivative of the first pattern signal with respect to one of the first profile parameters.

9. The apparatus of claim 8, wherein the optical system is further configured to illuminate a first stack target with radiation and detect scattered radiation to obtain a first stack signal and to illuminate a second stack target with radiation and detect scattered radiation to obtain a second stack signal, and wherein the processor is further configured to use, in the calculation, a difference between the first stack signal and the second stack signal, thereby to reduce an influence of variations between stacks underlying the pattern targets.

10. The apparatus of claim 9, wherein the processor is further configured to calculate values of differential stack parameters using the difference between the first stack signal and the second stack signal and predetermined information as to a dependence of at least one of the first and second stack signals on stack parameters and is further configured to use the calculated values of differential stack parameters, in the calculating values of differential pattern profile parameters.

11. A non-transitory computer program product comprising machine-readable instructions for causing a processor to perform operations comprising:
   obtaining a first patterned signal corresponding to detected scattered radiation from a first pattern target having first profile parameters;
   obtaining a second patterned signal corresponding to detected scattered radiation from a second pattern target, different than the first pattern target and having second profile parameters; and
   calculating values of differential pattern profile parameters using a difference between the first pattern signal and the second pattern signal,
   wherein the differential pattern profile parameters are differences between the first and second profile parameters, and
   wherein the calculating comprises using predetermined information, the predetermined information comprising a first or a higher order derivative of the first pattern signal with respect to one of the first profile parameters.

12. A lithographic system comprising:
a lithographic apparatus comprising:
an illumination optical system configured to illuminate a pattern; and
a projection optical system configured to project an image of the pattern onto a substrate; and
an inspection apparatus, comprising:
an optical system configured to illuminate one or more pattern targets with radiation and detect scattered radiation to obtain a corresponding pattern signal; and
a processor configured to calculate values of differential pattern profile parameters using a difference between a first pattern signal detected from a first pattern target having first profile parameters using the optical system and a second pattern signal detected from a second pattern target, different than the first pattern target and having second profile parameters, using the optical system,
wherein the differential pattern profile parameters are differences between the first and second profile parameters,
wherein the calculating comprises using predetermined information, the predetermined information comprising a first or a higher order derivative of the first pattern signal with respect to one of the first profile parameters, and
wherein the lithographic apparatus is configured to use the values of differential pattern profile parameters from the inspection apparatus in applying the pattern to further substrates.

13. A non-transitory computer-readable storage device having computer-executable instructions stored thereon, execution of which, by a computing device, causes the computing device to perform operations comprising:
obtaining a first patterned signal corresponding to detected scattered radiation from a first pattern target having first profile parameters;
obtaining a second patterned signal corresponding to detected scattered radiation from a second pattern target, different than the first pattern target and having second profile parameters; and
calculating values of differential pattern profile parameters using a difference between the first pattern signal and the second pattern signal,
wherein the differential pattern profile parameters are differences between the first and second profile parameters, and
wherein the calculating comprises using predetermined information, the predetermined information comprising a first or a higher order derivative of the first pattern signal with respect to one of the first profile parameters.

14. A lithographic system comprising:
a lithographic apparatus comprising:
an illumination optical system configured to illuminate a pattern; and
a projection optical system configured to project an image of the pattern onto a substrate; and
an inspection apparatus comprising:
an optical system configured to illuminate one or more pattern targets with radiation and to detect scattered radiation to obtain a corresponding pattern signal; and
a processor configured to calculate values of differential pattern profile parameters using a difference between a first pattern signal detected from a first pattern target having first profile parameters using the optical system and a second pattern signal detected from a second pattern target, different than the first pattern target and having second profile parameters, using the optical system,
wherein the differential pattern profile parameters are differences between the first and second profile parameters, and
wherein the first and second profile parameters comprise at least one of a critical dimension, a side wall angle, and a resist height.

15. A method of manufacturing devices wherein a device pattern is applied to a series of substrates using a lithographic process, the method comprising:
inspecting at least one periodic structure formed as part of, or beside, the device pattern on at least one of the substrates using a method comprising:
illuminating a first pattern target having first profile parameters with radiation and detecting scattered radiation to obtain a first pattern signal;
illuminating a second pattern target, different than the first pattern target and having second profile parameters, with radiation and detecting scattered radiation to obtain a second pattern signal; and
calculating values of differential pattern profile parameters using a difference between the first pattern signal and the second pattern signal,
wherein the differential pattern profile parameters are differences between the first and second profile parameters, and
wherein the first and second profile parameters comprise at least one of a critical dimension, a side wall angle, and a resist height; and
controlling the lithographic process for later substrates in accordance with the result of the inspecting method.

16. The method of claim 1, wherein the first and second profile parameters comprise at least one of a critical dimension, a side wall angle, and a resist height.

* * * * *